United States Patent [19]
Rinehart et al.

[11] Patent Number: 5,514,708
[45] Date of Patent: May 7, 1996

[54] **CYTOTOXIC METABOLITES FROM *MYRIAPORA TRUNCATA***

[75] Inventors: Kenneth L. Rinehart; Jie-Fei Cheng; Jong-Soo Lee, all of Urbana, Ill.

[73] Assignee: PharmaMar, S.A., Madrid, Spain

[21] Appl. No.: 198,444

[22] Filed: Feb. 18, 1994

[51] Int. Cl.$^6$ .................. A61K 31/35; A61K 31/335; C07D 309/10; C07D 303/32
[52] U.S. Cl. .................. 514/460; 514/475; 549/414
[58] Field of Search .................. 549/414, 556; 514/460, 475

[56] References Cited

PUBLICATIONS

Wasserman, et al., "Application of the Carbonyl Epoxide Rearrangement to the Formation of Dioxabicycloalkanes Alkenes. Synthesis of the *Mus Musculus* Pheromone.", *Tetrahedron Letters*, vol. 27, No. 40, pp. 4909–4912, 1986.
Schmitz, et al., "Tedanolide: A Potent Cytotoxic Macrolide from the Caribbean Sponge *Tedania ignis*", *J. Am. Chem. Soc.*, 1984, vol. 106, pp. 7251–7252.
Wilson, et al., "Zaragozic Acid A, A Potent Inhibitor of Squalene Synthase: Initial Chemistry and Absolute Stereochemistry", *J. Org. Chem.*, 1992, vol. 57 pp. 7151–7158.
Fusetani, et al., "Cytotoxic Metabolites of the Marine Sponge *Mycale adhaerens* Lambe", *J. Org. Chem.*, 1991, vol. 56, 4971–4974.
Pretsch, et al., "Tables of Spectral Data for Structure Determination of Organic Compounds", Springer–Verlag, Berlin, Heidelberg, New York, Tokyo, 1983, p. H190.
C. Christophersen, "Secondary Metabolites from Marine Bryozoans. A Review", *Acta Chemica Scandinavica*, vol. 39,(1985), pp. 517–529.
Witten, et al., "Structures of Two Cockroach Neuropeptides Assigned by Fast Atom Bombardment Mass Spectrometry", *Biochemical and Biophysical Research Communications*, vol. 124, No. 2, 1984, pp. 350–358.
D. J. Faulkner, "Marine Natural Products", vol. 10, No. 5, Oct. 1993, pp. 497–539.
Casadevall, et al., "Progress in the Chemistry of Organic Natural Products", vol. 57, 1991, pp. 155–195.

*Primary Examiner*—Nicky Chan
*Attorney, Agent, or Firm*—Ernest V. Linek

[57] ABSTRACT

The present invention is based upon the discovery that the methanol extract of the bryozoan *Myriapora truncata* showed potent cytotoxicity against L1210 murine leukemia cells (99% inhibition at 50 µg/mL). Fractionation and purification of active components from this extract, guided by a cytotoxicity assay, resulted in the isolation of a novel, highly cytotoxic polyketide-derived metabolite MT-332 (Compound 3) and its equilibrium isomer (Compound 4), along with two less active compounds, MT-381 (Compound 1) and MT-381-B (Compound 2). The equilibrium mixture of Compounds 3 and 4 showed 88% inhibition at 0.2 µg/mL against L1210 cells.

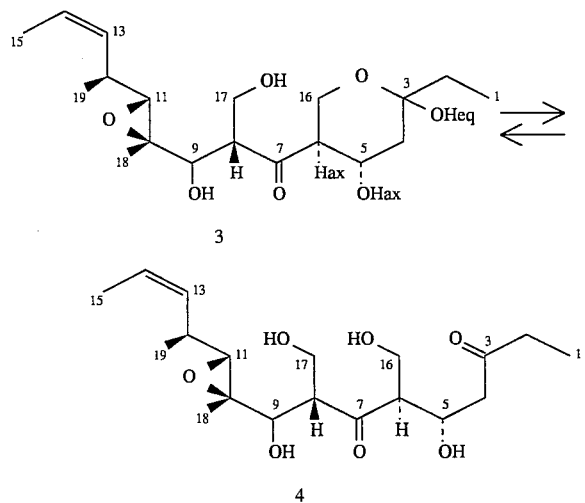

3 Claims, No Drawings

CYTOTOXIC METABOLITES FROM *MYRIAPORA TRUNCATA*

BACKGROUND OF THE INVENTION

Bryozoans are a group of primitive colonial animals widely distributed throughout the world's marine and freshwater environments (see Reference 1(a), infra). Chemical research on their biologically active metabolites, however, has been limited (see References 1(a) and 1(b), infra). Among those metabolities previously isolated from marine bryozoans, bryostatins from *Bugula neritina* are the most exciting and promising compounds, which exhibit pronounced cytotoxicity as well as immunomodulation or protein kinase C activation (see Reference 2).

SUMMARY OF THE INVENTION

It has been discovered that the methanol extract of the bryozoan *Myriapora truncata*, collected in the Western Mediterranean, is highly active against L1210 murine leukemia cells (99% inhibition at 50 µg/mL). As such, it is believed that the compounds responsible for this in vitro activity will be useful as antitumor agents in vivo, particularly against mammalian tumors, and most particularly those tumors selected from the group consisting of leukemia, melanoma and nasopharyngeal cancer. Fractionation and purification of active components from this extract, guided by a cytotoxicity assay, resulted in the isolation of a novel, cytotoxic polyketide-derived metabolite, designated herein as MT-332; which is an equilibrium mixture of a hemiketal and a free hydroxy ketone whose structures are shown below as Compounds 3 and 4.

The equilibrium mixture (Compounds 3 and 4) showed 88% inhibition at 0.2 µg/mL against L1210 cells. Two other less active, but structurally related compounds (designated herein as Compounds 1 and 2, and/or MT-381 and MT-381-B, respectively) were also isolated from the same organism and their structures are shown below. Compound 1 was active at 0.5 µg/mL against L1210 cells and Compound 2 was 70% active at 5 µg/mL against L1210 cells.

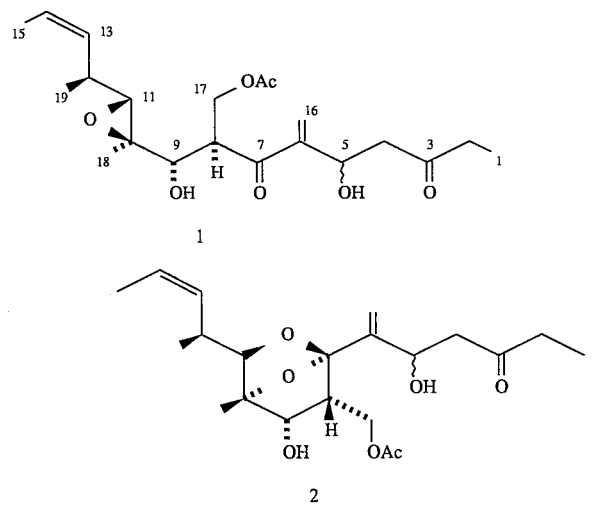

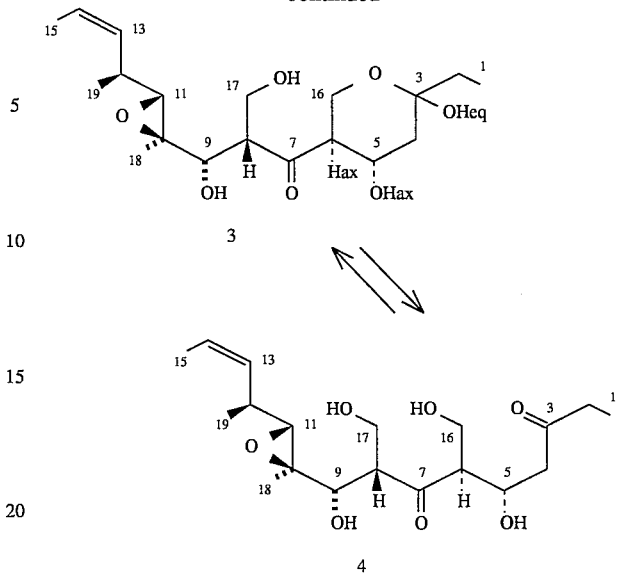

DETAILED DESCRIPTION OF THE PREFERRED EMBODIMENTS

During a systematic screening for pharmaceutically active compounds from Mediterranean Sea marine organisms, the present inventors discovered that the methanol extract of the bryozoan *Myriapora truncata* showed potent cytotoxicity against L1210 murine leukemia cells (99% inhibition at 50 µg/mL). Fractionation and purification of active components guided by a cytotoxicity assay resulted in the isolation of a novel, highly cytotoxic polyketide-derived metabolite MT-332 (Compound 3) and its equilibrium isomer (Compound 4), along with two less active compounds, MT-381 (Compound 1) and MT-381-B (Compound 2). The equilibrium mixture of Compounds 3 and 4 exhibited 88% inhibition at 0.2 µg/mL against L1210 cells.

As described above, the compounds of the present invention are active against L1210 mouse leukemia cells. Thus, it is believed that these cytotoxic compounds will be useful as antitumor compounds in animals and preferably as antileukemic agents in humans. When being used as cytotoxic or antileukemic agents, the compounds of the present invention can be prepared and administered in various dosage forms, especially parenteral dosage forms. It will be clear to those having ordinary skill in this art that the dosage forms may comprise, as the active ingredient, one or more of the compounds of the present invention. The skilled artisan will likewise recognize that the dosages and routes of administration will vary according to the needs of the patient and the specific activity of the active ingredient(s). The determination of these parameters is within the ordinary skill of the practicing physician.

The present invention is thus directed to the method of isolating these compounds, the determination of their structures and stereochemistry, and the use thereof as active ingredients in pharmaceutical compositions.

Physical Properties of the Compounds of the Invention

The IR spectrum of Compound 1 showed absorptions at 3580, 1747, 1709 and 1280 cm$^{-1}$, the first three attributable to hydroxyl, ester and ketone functional groups, respectively. FABMS gave an [M+H]+ ion at m/z 397 and several deacetyl or dehydrated fragment ions at m/z 355, 337, and 319. HRCIMS gave the molecular formula $C_{21}H_{32}O_7$ for Compound 1, (found 397.2239, calcd. for M+H, 397.2226, Δ-1.3 mDa). $^1$H NMR in $CDCl_3$ (Table 1, below) indicated 32 proton signals among which two ($\delta_H$ 2.63, d, 5.5 Hz and 3.63, d, 5.5 Hz) are exchangeable hydroxyl protons. $^{13}$C NMR (Table 1) showed all required 32 carbons including two ketone carbonyls, one ester carbonyl, four olefinic carbons, five methyls, three $sp^3$ methylenes, five $sp^3$ methines, and one quaternary carbon.

Scheme I

Partial structures A–D for 1 by COSY and HMQC

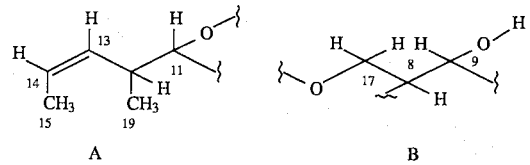

A          B

TABLE 1

NMR data for MT381(1) and MT381-B(2)

| | MT381(1) | | | | MT381B(2) | |
|---|---|---|---|---|---|---|
| atom # | CDCl₃ | | | CD₃OD | CD₃OD | CD₃CN |
| 1 | 7.45 CH₃ | 1.05 t, 7.0 | 7.86 | 1.02 t, 7.5 | 7.93 1.02 t, 7.0 | 0.96 t, 7.5 |
| 2 | 36.57 CH₂ | 2.44, m | 37.17 | 2.50 m | 37.39 2.50 m | 2.44 m |
| 3 | 211.61 C | | 211.83 | | 212.67 | |
| 4 | 47.90 CH₂ | 2.52 dd, 18.0, 9.0 | 50.33 | 2.44 dd, 16.0, 9.5 | 49.61 2.70 dd, 16.5, 9.5 | 2.52 dd, 16.0, 9.0 |
| | | 2.88 dd, 17.5, 3.0 | | 2.65 dd, 16.0, 3.0 | 3.05 dd, 16.5, 2.5 | 2.97 dd, 16.5, 2.5 |
| 5 | 66.30 CH | 4.97 m | 66.71 | 5.02 dd, 3.0, 9.5 | 67.71 4.71 dd, 10.5, 1.0 | 4.60 brm |
| 6 | 150.38 C | | 153.88 | | 146.69 | |
| 7 | 202.45 C | | 202.91 | | 109.48 | |
| 8 | 46.61 CH | 3.75 m | 49.61 | 3.76 dt, 4.0, 10.0 | 51.11 2.76 q, 7.0 | 2.70 q, 7.0 |
| 9 | 75.72 CH | 3.53 m | 77.50 | 3.34 d, 10.0 | 71.90 4.21 d, 7.0 | 4.15 t, 7.0 |
| 10 | 62.76 C | | 64.15 | | 89.39 | |
| 11 | 66.23 C | 2.74 d, 9.5 | 67.55 | 2.64 d, 9.5 | 87.15 3.28 d, 10.0 | 3.27 d, 10.5 |
| 12 | 31.20 CH | 2.42 m | 32.34 | 2.50 m | 35.18 2.50 m | 2.44 m |
| 13 | 129.98 CH | 5.23 dt, 1.5, 10.5, 10.5 | 131.54 | 5.27 dt, 2.0, 10.0, 10.0 | 132.54 5.18 dt, 1.5, 10.5, 10.5 | 5.16 dt, 2.0, 10.5, 10.5 |
| 14 | 125.04 CH | 5.51 dq 10.5, 7.0 | 126.09 | 5.50 m | 124.92 5.50 dq, 10.5, 7.0 | 5.48 dt, 7.0, 10.5 |
| 15 | 13.34 CH₃ | 1.62 d, 7.0 | 13.59 | 1.65 dd, 7.0, 1.5 | 13.33 1.66 dd, 2.0, 7.0 | 1.66 dd, 2.0, 7.0 |
| 16 | 126.93 CH₂ | 6.28 s | 126.57 | 6.22 d, 1.5 | 113.13 5.41 d, 1.5 | 5.32 d, 1.0 |
| | | 6.23 s | | 6.28 s | 5.42 s | 5.34 s |
| 17 | 63.07 CH₂ | 4.32 dd, 11.0, 4.5 | 64.36 | 4.32 dd, 4.0, 11.0 | 62.62 4.08 dd, 11.5, 7.5 | 3.94 dd, 11.0, 7.0 |
| | | 4.06 t, 11.0 | | 3.88 t, 11.0 | 3.84 dd, 11.5, 7.0 | 3.75 dd, 11.0, 7.0 |
| 18 | 12.08 CH₃ | 1.34 s | 11.65 | 1.38 s | 11.45 1.40 s | 1.33 s |
| 19 | 18.60 CH₃ | 1.12 d, 6.5 | 18.81 | 1.10 d, 7.0 | 18.91 1.02 d, 6.5 | 0.98 d, 6.5 |
| 20 | 170.34 C | | 172.08 | | 173.10 | |
| 21 | 20.74 CH₃ | 1.99 s | 20.65 | 1.94 s | 20.23 2.02 s | 1.96 s |
| 5-OH | | 3.63 d, 5.5 | | exchanged | exchanged | 3.17 brs |
| 9-OH | | 2.63 d, 5.5 | | exchanged | exchanged | 3.12 d, 7.0 |

Four separated partial structures A-D (Scheme I) accounting for 15 carbons and 26 protons for Compound 1 were readily identified by COSY and HMQC data taken in $CDCl_3$. A cis double bond in partial structure A was deduced from the coupling constant (J=10 Hz). In the COSY spectrum, a methine proton at $\delta_H$ 3.75 (H-8) was found to couple with the oxygenated methylene protons at $\delta_H$ 4.32 and 4.06 (H2-17) and an oxygenated methine proton at $\delta_H$ 3.53 (H-9), respectively (partial structure B). In partial structure C, two singlet olefinic protons at $\delta_H$ 6.23 and 6.28 were assigned to terminal double bond protons, which showed cross peaks in a COSY spectrum with the methine proton H-5 ($\delta_H$ 4.97). The latter was coupled with the methylene at $\delta_H$ 2.52 and 2.58 (H₂-4). Two hydroxyl groups were located at C-9 and C-5 on the basis of the coupling of hydroxyl protons with H-9 and H-5 respectively.

-continued
Scheme I

Partial structures A–D for 1 by COSY and HMQC

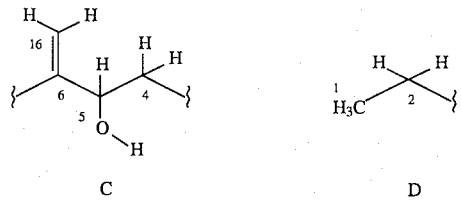

C          D

The deshielded singlet methyl at $\delta_H$ 1.99 ($\delta_C$ 20.74) in combination with the ester carbonyl ($\delta_C$ 170.34, IR 1747, 1280 $cm^{-1}$) indicated the presence of an acetyl group. Thus two ketone carbonyls ($\delta_C$ 211.62 and 202.45), a singlet methyl group ($\delta_H$ 1.34s, $\delta_C$ 12.08) and an oxygenated quaternary carbon ($\delta_C$ 62.76) remained to be assigned. In the HMBC spectrum (Scheme II), cross peaks from the singlet methyl group at $\delta_H$ 1.34 to the quaternary carbon at $\delta_C$ 62.76 (C-10) and long range couplings from H-9 to the same quaternary carbon and C-11 ($\delta_C$ 66.23) in partial structure C were observed. Accordingly, partial structures A and B could be linked through the C-10 quaternary carbon with a methyl attached. An epoxide was assigned at C-10 and C-11 based on the upfield $^{13}C$ and/or $^1H$ chemical shifts (Table I). An acetyl group was readily recognized at C-17 from the deshielded $H_2$-17 proton resonances and the HMBC correlations for H-17a and H-17b to the ester carbonyl. Similarly, spin systems B and C were connected via a carbonyl group at $\delta_C$ 202.45 which is correlated to protons H-8 ($\delta_H$ 3.75), $H_2$-17 in the partial structure B and terminal olefin protons $H_2$-16 ($\delta_H$ 6.23 and 6.28) in the partial structure C. Although only terminal ethyl group D was found to be correlated with the remaining carbonyl ($\delta_C$ 211.6) in the HMBC spectrum, the bond connection between C-4 and the C-3 carbonyl is the only way to complete the structure assignment (Scheme II). The chemical shifts and coupling patterns of $H_2$-4 ($\delta_H$ 2.52 and 2.88) are compatible with the structure assigned Compound 1 (Scheme I). From the biogenetic point of view, it is worth noting that the structure assigned Compound 1 is similar to the side chain part of tedanolide (Compound 5, see Reference 3), a macrolide isolated from the Caribbean marine sponge *Tedania ignis* with potent cytotoxicity. Interestingly, two structurally related $C_{19}$ polyketide-derived lactones, named octalactins A and B, have been reported from a marine microorganism (Streptomyces) isolated from the surface of a gorgonian (see Reference 4).

Compound 2, originally isolated from the natural extract of the specimen, was also detected during NMR measurement of pure Compound 1 in $CDCl_3$. Unlike Compound 1, Compound 2 didn't show any UV absorption above 210 nm. The IR absorptions at 3580, 1747 and 1233 $cm^{-1}$ are similar to those of Compound 1, indicating the presence of similar hydroxyl, ester and/or ketone functional groups. FABMS exhibited the same $[M+H]^+$ ion as MT-381 (Compound 1) at m/z 397 as well as $[M+Na]^+$ (m/z 419) and $[M+K]^+$ (m/z 435) ions. The same molecular formula of $C_{21}H_{32}O_7$ for Compound 2 was determined by HRFABMS (Found: 397.2135, calcd. for $C_{21}H_{33}O_7$ $[M+H]^+$: 397.2226, $\Delta$+9.1 mDa; found 419.2052, calcd. for $C_{21}H_{32}O_7Na$, 419.2045, $\Delta$-0.7 mDa; and found 435.1780, calcd. for $C_{21}H_{32}O_7K$, 435.1785, $\Delta$+0.5 mDa).

The $^1H$ NMR spectrum of Compound 2 is different from that of Compound 1 in coupling constants and, primarily, in the chemical shifts. The prominent shifts were observed for protons around C-7 such as those at C-8, C-9, C-11 and C-16 (see Table I). The carbon framework, however, is identified to be the same as that of Compound 1 based on the analyses of coupling constants and COSY correlation. $^{13}C$ NMR data (see Table I) for these two compounds, on the other hand, showed remarkable differences. One of two carbonyl groups, at $\delta_C$ 202.91 (in $CD_3OD$) originally observed in Compound 1 (C-7) has been replaced by a ketal quaternary resonance at $\delta_C$ 109.48. Moreover, the chemical shifts for C-10 and C-11 were found to be shifted dramatically downfield from $\delta_C$ 64.15 and 67.55 to $\delta_C$ 71.90 and 89.39, respectively, which are reasonably assigned to two oxygenated carbons with a ring larger than an epoxide. These data suggest that the carbonyl oxygen at C-7 has attached at the epoxide on C-10 and C-11 to form a 2,7-diaxabicyclo [2.2.1]heptane skeleton. The HMBC spectrum indicated long-range $^1H$-$^{13}C$ coupling for terminal double bond protons ($H_2$-16) to the ketal carbon at $\delta_C$ 109.48, which could not be more than three bonds away from $H_2$-16 and should be placed at C-7. Thus the structure of MT-381-B could be assigned as Compound 2 (Scheme III). The intramolecular ring opening of γ,δ-epoxy or δ,ε-epoxy ketones to provide the dioxabicyclo skeleton seems to be a quite common process in the presence of trace acids or Lewis acids (see Reference 5).

Scheme II

Selective long range $^1H$–$^{13}C$ correlations for 1 revealed by HMBC

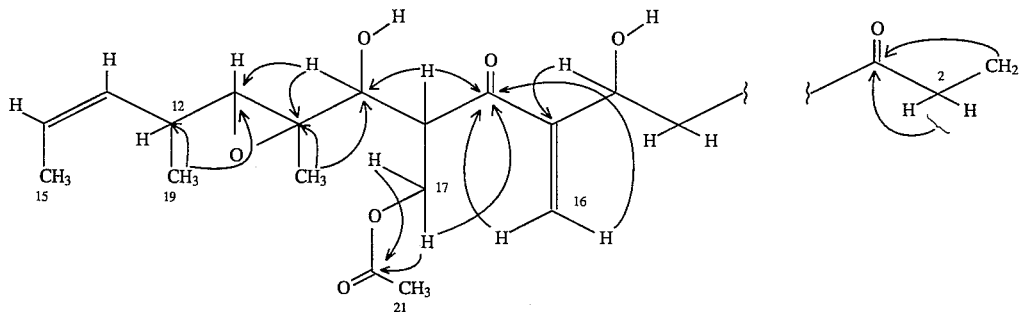

Scheme III

Structures 1 and 2.

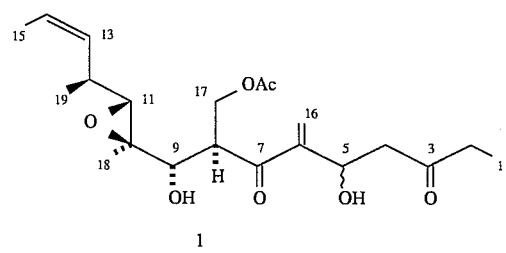

-continued
Scheme III

Structures 1 and 2.

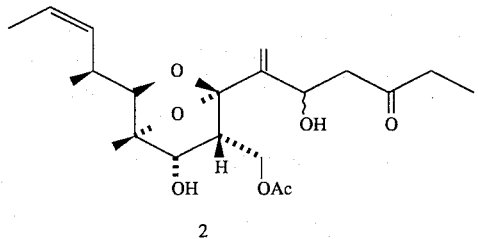

2

The relative stereochemistry for Compound 1 and Compound 2 was mostly assigned on the basis of NOE experiments conducted with MT-381-B (Compound 2) and by comparison of their coupling constants with tedanolide (Compound 5). The proton coupling constant between H-8 and H-9 in Compound 2 is 7 Hz, implying the endo-endo cis relationship for these two protons (see References 6 and 7). Further evidence supporting this assignment arose from the observation of NOE cross peaks in the ROESY spectrum for H-9 to H-8, H-12 and H$_3$-15, which in turn located the cis olefin group (C-12-C-15) in the same endo face and the H-11 proton at the exo position. The relative stereochemistry at C-11 and C-12 could be assigned as follows. The dihedral angle between H-12 and H-11 seems to be near 180° or 0° due to their relatively large coupling constant (10 Hz). Observation of NOE cross peaks for protons H$_3$-19/H-11 and H-12, and H$_3$-15/H-9 justified the spatial proximity of H-12 to H-9 and H$_3$-19 to H-11. Thus the relative stereochemistry for H-11 and H-12 was assigned as trans. The relative stereochemistry for six contiguous chiral centers (C-7-C-12) in Compound 2 could therefore be assigned as 7S, 8R, 9S, 10S, 11R, 12S, or its mirror image (Scheme IV). Intramolecular attack of a carbonyl oxygen at γ,δ-epoxide would invert the configuration at the γ-position. Accordingly, its cyclization precursor (Compound 1) should possess the 8R*, 9S*, 10R*, 11R*, 12S* relative configurations (see Scheme III).

The stereochemistry at C-5 in both compounds could not be assigned by the NOE experiments.

Scheme IV

NOE observed by difference NOE and/or ROESY

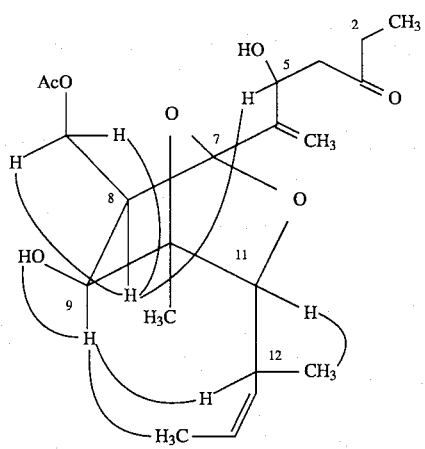

A comparison of coupling constants of Compound 1 and tedanolide (Compound 5) assists in the assignment of relative stereochemistry due to the similarity of these two compounds. As can be seen in Table 2, the coupling constants among protons at C-8-C-15 in Compound 1 are almost identical with those at C-16-C-23 in Compound 5. The relative configurations at C-8-C-15 were thus confirmed to be the same as in the tedanolide sidechain, Compound 1 i.e., 8R*, 9S*, 10R*, 11R*, 12S*.

TABLE 2

Comparison of coupling constants of Compounds 1 and 3 and the tedanolide side chain (Compound 5) in Hz

|    | H8/9 | H8/1 | H11/12 | H12/13 | H13/14 | H14/15 | H13/15 | H12/19 |
|----|------|------|--------|--------|--------|--------|--------|--------|
| 1  | 10   | 11   | 9.5    | 10.0   | 10.0   | 7.0    | 1.5    | 6.7    |
| 3  | 9.7  | —    | 9.2    | 10.0   | 10.0   | 7.0    | 1.5    | 6.8    |
| 5* | 9.5  | 11.6 | 9.4    | 10.8   | 10.8   | 7.4    | 1.7    | 6.5    |

*Refer to MT numbering

Structure of MT-332 (Compound 3) and its Isomer (Compound 4)

The most cytotoxic constituent of *Myriapora truncata* was isolated as a mixture of two equilibrium isomers, designated herein as Compounds 3 and 4. Their dynamic nature and small amounts made the isolation and characterization of these active components quite difficult. The major isomer is hemiketal MT-332 (Compound 3) and the minor the hydroxyl ketone form (Compound 4) with a relative ratio of 3:1 as determined by $^1$H NMR. These two compounds are believed to be physically inseparable and they could only be recognized in the COSY spectrum.

FABMS of the MT-332 mixture (Compounds 3 and 4) didn't give the [M+H]$^+$ ion peak but showed an [M+Na]$^+$ peak at m/z 395, an [M+K]$^+$ peak at m/z 411 and a doubly dehydrated fragment ion at m/z 337 as well. Tandem MS/MS experiments on peaks at 411 and 395 confirmed the presence of K$^+$ and Na$^+$ ions in these two pseudo-molecular ion peaks, respectively. Thus the molecular weight of the MT-332 mixture was concluded to be 372 Daltons. HRFABMS established the common molecular composition of Compounds 3 and 4 as C$_{19}$H$_{32}$O$_7$ (found 411.1784, calcd. for C$_{19}$H$_{32}$O$_7$K, 411.1785, Δ+0.1 mDA; found 395.2054, calcd. for M+Na, C$_{19}$H$_{32}$O$_7$Na, 395.2045, Δ-0.9 mDA; found 337.2019, calcd. for M+H-2H$_2$O, 337.2015, Δ-0.4 mDA).

The $^1$H NMR spectrum of this mixture shared many common characteristics with MT-381 (Compound 1) such as a terminal ethyl group, C-15, C-18, and C-19 methyls, and the C-13/C-14 cis double bond. A doublet epoxide methine proton, H-11 (δ$_H$ 2.61 d, 9.2 Hz), was also observed for Compounds 3 and 4. On the other hand, terminal olefinic protons and acetyl methyl protons were no longer present in the $^1$H NMR spectrum of the mixture of Compounds 3 and 4. The modification should therefore have taken place at C-17 and C-16 with respect to MT-381 (Compound 1). COSY and coupling constant analyses identified four separated spin networks for both Compounds 3 and 4. Three of them are formally identical with partial structures A, B, and D, of Compound 1 (cf. Scheme I). The chemical shifts and coupling constants indicated the remaining one partial structure (C' for Compound 3 and C" for Compound 4) was a 4-carbon unit (Scheme V).

Scheme V

Partial structures of 3(C') and its equilibrium isomer 4(C")

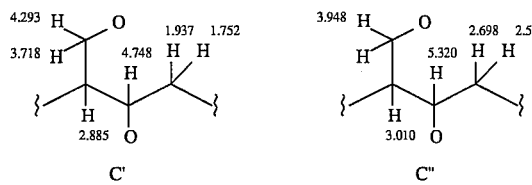

It is apparent from a comparison of the partial structures of Compound 1 with Compounds 3 or 4, that the difference between these compounds is in the replacement of a terminal C-16 double bond with a CH$_2$OR group. By parallel arguments with MT-381 (Compound 1) and taking into consideration the $^1$H NMR and FABMS data, it is reasonable to postulate two carbonyls (C-3,C-7) and an oxygenated quaternary carbon (C-10) to connect four fragments, although the sample amount made it impossible to record a complete decoupled $^{13}$C NMR spectrum with good signal to noise ratio. Two quaternary carbons at $\delta_C$ 98.41 and 54.65 were clearly observed, which may be assigned to a hemiketal carbon and an oxygenated carbon, respectively. Again, HMQC and HMBC spectra are quite informative. Those carbons with protons attached have been detected by HMQC experiments. The long range couplings for singlet methyl protons at $\delta_H$ 1.334 to C-9 ($\delta_C$ 78.08), C-11 ($\delta_C$ 67.87) and the quaternary carbon at $\delta_C$ 64.25 have been observed in the HMBC spectrum, which definitely indicated the presence of the C-8-C-15 unit, with an epoxide on C-10 and C-11. That the C-16 hydroxyl group and C-3 carbonyl have cyclized to form a six-membered hemiketal in Compound 3 was evident from the upfield proton chemical shifts (Table 3) for H$_3$-1 ($\delta_H$ 0.910), H$_2$-2 ($\delta_H$ 1.575) and H$_2$-4 ($\delta_H$ 1.947 and 1.75) as compared to those in Compound 1. The HMBC cross peak for the terminal ethyl's methyl ($\delta_H$ 0.91) to the hemiketal carbon at $\delta_C$ 98.41 justified the above assignment. Finally, the chemical shifts of C-6 ($\delta_C$ 56.08, $\delta_H$ 2.89) and C-8 ($\delta_C$ 40.50, $\delta_H$ 3.28) methines implied the presence of a carbonyl at C-7, which accounted for the remaining one carbon, one oxygen and one degree of unsaturation.

For the minor component, $^1$H NMR for the left part (H-8-H-15, and H-17-H-19) was like that of Compound 3. The difference was recognized in the right part, i.e., partial structure C" and a terminal ethyl group. The downfield chemical shifts for H-2 and H-4 in Compound 4 suggested the presence of a C-3 carbonyl rather than a hemiketal group. A weak but clear long range coupling for the terminal ethyl's methyl ($\delta_H$ 0.99) to the carbonyl at $\delta_C$ 212.69 was present in an HMBC spectrum. Thus the structure was assigned as Compound 4.

TABLE 3

| atom | $\delta_H$ | m | J | $\delta_c{}^a$ |
|---|---|---|---|---|
| 1 | 0.91 | t | 7.3 | 7.7 |
| 2 | 1.57 | q | 7.3 | 35.12 |
| 3 | | | | 98.41[b] |
| 4 | 1.94 | dd | 3.3, 14.0 | 38.65 |
|   | 1.75 | dd | 2.9, 14.0 | |
| 5 | 4.76 | brm | | 65.83 |

TABLE 3-continued $^1$H and $^{13}$C NMR data for MT-332 ($\delta$ ppm, J Hz)

| atom | $\delta_H$ | m | J | $\delta_c{}^a$ |
|---|---|---|---|---|
| 6 | 2.89 | m | | 56.08 |
| 7 | c | | | c |
| 8 | 3.28 | m | | 40.50 |
| 9 | 3.16 | d | 9.7 | 78.08 |
| 10 | | | | 64.25[b] |
| 11 | 2.61 | d | 9.2 | 67.87 |
| 12 | 2.48 | m | | 32.21 |
| 13 | 5.29 | dd | 10.0 | 131.42 |
| 14 | 5.54 | dq | 10.0, 7.0 | |
| 15 | 1.65 | d | 7.0 | 13.32 |
| 16 | 4.29 | dd | 1.6, 11.6 | 56.70 |
|    | 3.72 | dd | 3.9, 11.6 | |
| 17 | 3.64 | dd | | 61.68 |
| 18 | 1.34 | s | | 11.25 |
| 19 | 1.09 | d | 6.8 | 18.51 |

[a]detected by HMQC;
[b]detected by $^{13}$C NMR;
[c]not detected.

The relative stereochemistry at C-8-C-12 in Compounds 3 or 4 was assigned as the same as that of MT-381 (Compound 1) or the tedanolide side chain on the basis of coupling constant comparisons (Table 2). Since H$_2$-16 was at $\delta_H$ 4.29 and 3.72 with coupling constants of 11.6, 11.6 and 3.9, 11.6 Hz, respectively, H-6 was assigned to be axial. Similarly, the coupling constants between H-4 and H-5 are 3.3 and 2.9 Hz, indicating the proton H-5 should be equatorial. Thus the relative stereochemistry for H-5 and H-6 is concluded to be trans. The hemiketal hydroxyl group at C-3 was arbitrarily placed equatorial in order to avoid an unfavorable 1,3-diaxial interaction between hydroxyl groups at C-3 and C-5.

Scheme VI

Structures of MT-332(3), 4, and tedanolide (5)

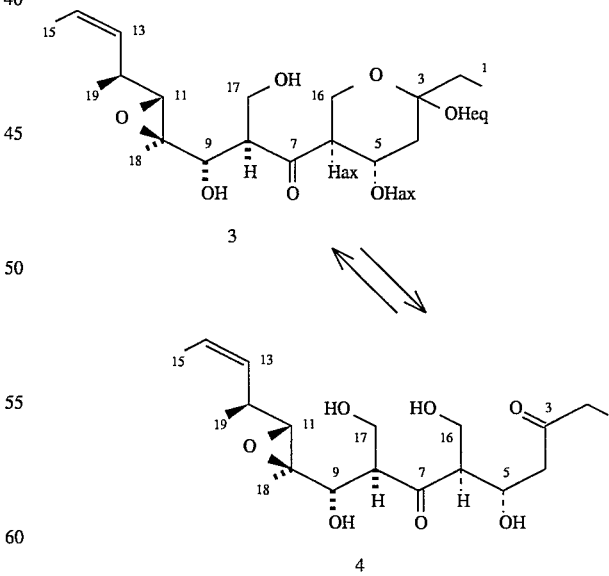

-continued
Scheme VI

Structures of MT-332(3), 4, and tedanolide (5)

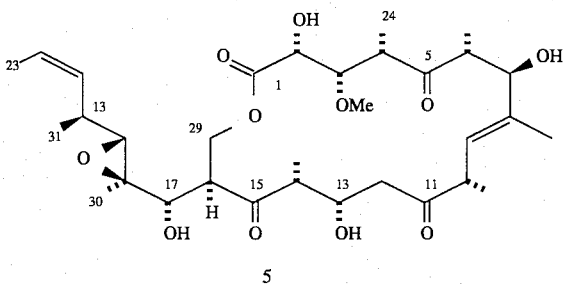

5

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

General Methods:

Optical rotations were measured on a Jasco DIP 370 polarimeter. UV spectra were taken on a Perkin-Elmer Lamda-3 spectrometer. Infrared spectra were taken on an IBM IR/32 FTIR spectrometer using $CCl_4$ solutions. $^1H$ and $^{13}C$ NMR spectra were recorded on a GN 500 or Unity 400 spectrometer in $CD_3OD$, $CD_3CN$, or $CDCl_3$ as indicated. The 3.30 ppm resonance of $CD_2HOD$ and 49.0 ppm resonance of $CD_3OD$ were used as internal references for $^1H$ and $^{13}C$ NMR spectra respectively. A $^1H$ selected probe for inverse experiments was used for HMBC and HMQC measurements. Both low and high resolution FAB mass spectra were obtained on a VG 70 SE-4F spectrometer using magic bullet as matrix (see Reference 8). Tandem MS (FABMS/CID/MS) spectra were recorded on a VG 70 SE-4F spectrometer. High resolution CI mass spectra were obtained on a VG 70 VSE spectrometer.

As used herein, FABMS stands for "fast atom bombardment mass spectrometry"; HRCIMS stands for "high resolution chemical ionization mass spectrometry" COSY stands for "correlation spectrometry"; HMQC stands for "heteronuclear multiple quantum correlation"; HBMC stands for "heteronuclear multiple bond correlation"; HRFABMS stands for "high resolution fast atom bombardment mass spectrometry"; NMR stands for "nuclear magnetic resonance spectroscopy"; NOE stands for "nuclear Overhauser effect"; ROESY stands for "rotating frame nuclear Overhauser spectrometry"; MT stands for "*Myriapora truncata*"; MS/MS stands for mass spectroscopy/mass spectroscopy; and MS(FABMS/CID/MS stands for "fast atom bombardment mass spectrometry/collisionally induced decomposition/mass spectrometry".

Collection, Extraction and Isolation:

The specimen of *Myriapora truncata* was collected at a number of sites in the Western Mediterranean Sea, including the Balearic Islands and Columbretes Islets, at Latitude 38°30', to 40°5'N, Longitude 0°15' to 4°15'E, at depths ranging from about 3 to 20 meters. Preliminary tests showed that the methanol extract of the specimen was highly active against L1210 cells (99% inhibition at 50 µg/mL and 87% inhibition at 25 µg/mL). Isolation of the active components was performed by following L1210 activity.

A frozen sample (1.3 kg) of *Myriapora truncata* was initially blended with MeOH and extracted three times with the same solvent to gave 23 g of crude extract after evaporation of the solvents. The combined methanol extracts were re-extracted with toluene and the toluene extract obtained exhibited 99% inhibition at 20 µg/mL against L1210 cells. The toluene soluble material was then partitioned between 80% aq. MeOH and hexane and the aqueous MeOH was further extracted with toluene, chloroform and n-BuOH.

High activity (ca. 96% inhibition at 5 µg/mL) was found for the toluene, chloroform and n-BuOH extracts, which were combined (total 1.4 g) and subjected to high speed counter current chromatography (Ito coil) with hexane-AcOEt-MeOH-water (1:4:2:3) as mobile phase to yield 36 fractions. Of these the most active fractions—tube numbers 4–18 (90% inhibition at 1 µg/mL, 120 mg) and tube numbers 19–25 (50% inhibition at 1 µg/mL, 56 mg) were combined and further fractionated over an HW-40 gel column using 50% aqueous MeOH as eluent. From 6 fractions collected, fraction 3 (tube numbers 11–15, 17 mg) showed the highest cytotoxicity (99% inhibition at 1 µg/mL), it was passed through a Sep-pak silica cartridge column ($CHCl_3$-MeOH: 95:5) followed by an ODS column to remove the polar components to afford the highly active compounds MT-332 (Compounds 3 and 4, 0.6 mg), and the less active Compound 1 (1.6 mg).

More MT-381 (Compound 1, 4.0 mg) and a mixture of Compounds 3 and 4 (0.6 mg) were isolated from a second batch of sample (1.41 kg) by the same isolation procedure. A trace amount of MT-381-B (Compound 2, 0.2 mg) was also isolated from this batch. The same compound was later detected during NMR measurement of MT-381 (Compound 1) in $CDCl_3$. Purification of decomposed products of MT-381 (4.0 mg) in an NMR tube was carried out by using HPLC with a Nucleosil column (1×25 cm, $CHCl_3$-MeOH: 100:3) followed by an Econosphere C8 U column (0.46×25 cm, 40% MeCN, $UV_{225}$ nm) to yield 1.3 mg of MT-381-B (Compound 2) and 2.4 mg of unchanged MT- 381 (Compound 1).

MT 381: UV (MeOH) $\lambda_{max}$ 217 ($\epsilon$16,200), 261 ($\epsilon$2400) nm: $[\alpha]^{26}_D$+71.07° (c. 0.242, MeOH): IR ($CCl_4$) $v_{max}$: 1228, 1709, 1747, 2359, 2935 and 3580 cm$^{-1}$; FABMS m/z 397 ($[M+H]^+$), 337 (M-HOAc), and 319 (M-HOAc-$H_2O$); HRCIMS found 397.2239, calcd. for $C_{21}H_{33}O_7$, 397.2226, Δ-1.3 mDa; $^1H$ and $^{13}C$ NMR data see Table 1.

MT-381-B; $[\alpha]_D^{26}$: –66.60° (c. 0.126, MeOH); IR ($CCl_4$) $v_{max}$: 1233, 1747, 2360, 2940 and 3580 cm$^{-1}$; FABMS m/z 397 $[M+H]^+$, 419 ($[M+Na]^+$) and 435 ($[M+K]^+$); HRFABMS found 397.2135, calc. for $C_{21}H_{33}O_7$, 397.2226, Δ+91 mDa; found 419.2052, calcd. for $C_{21}H_{32}O_7Na$, 419.2045, Δ-0.7 mDa and found 435.1780, calc. for $C_{21}H_{32}O_7K$, 435.1785, Δ+0.5 mDa; For $^1H$ and $^{13}C$ NMR data see Table 1.

MT-332: $[\alpha]_D^{26}$: (c. 0.06, MeOH); FABMS m/z 337 $(M+H-2H_2O)^+$, 395 ($[M+Na]^+$) and 411 ($[M+K]^+$); HRFABMS found 411.1784, calcd. for $C_{19}H_{32}O_7K$, 411.1785, Δ+0.1 mDa; found 395.2054, calcd. for M+Na, $C_{19}H_{32}O_7Na$, 395.2046, Δ-0.9 mDa; found 337.2019 calcd. for M+H-2H$_2$O, $C_{19}H_{29}O_5$, 337.2015, Δ-0.4 mDa); MS/MS: m/z 411→39; m/z 395→23; For $^1$H and $^{13}$C NMR data for Compound 3, see Table 3.

Alternate Isolation Process:

Crude methanol extract of *Myriapora truncata* (see above) was extracted with toluene. The active toluene fractions were combined and partitioned with AcOEt:hexane:MeOH:H$_2$O (7:4:4:3) and the partitioned upper phase was repeatedly extracted (2–3 times) with the lower phase. The lower phase was combined and chromatographed on a C-18 column. The column was developed and eluted with 60% MeOH, 80% MeOH and MeOH. The major activity was eluted with the 60% MeOH phase. This fraction showed 93.3% inhibition against L1210 cells at 1 μg/mL, and this fraction was further purified by HPLC (C-18 column, 75% MeOH as mobile phase, UV 230 nm as detection wavelength), to yield a fraction which exhibited 91.7% activity against L1210 cells at 0.2 μg/mL. It was later determined that 60% MeOH was a better mobile phase in this HPLC purification scheme. The purified fraction obtained using 60% MeOH exhibited 97.5% inhibition of L1210 cells at 0.2 μg/mL.

The following references, which have been cited above, are hereby incorporated herein by reference:

1. Reviews: (a) Christophersen, C., *Acta Chem. Scand. Ser. B*, 39, 517 (1985); (b) Faulkner, D. J., *Nat. Prod. Rep.*, 10, 497 (1993), and previous reports in the series.
2. Pettit, G. R., *Fortschr. Chem. Org. Naturst.*, ,57, 153 (1991).
3. Schmitz et al., *J. Am. Chem. Soc.*, 106, 7251 (1984). The C-17 configuration was misdrawn for tedanolide (loc. cit.) but 13-deoxytedanolide, isolated from the Japanese sponge *Mycale adhaerens*, was represented correctly by Fusetani et al., *J. Org. Chem.*, 56, 4971 (1991).
4. Tapiolas et al., *J. Am. Chem. Soc.*, 113, 4682 (1991).
5. Wasserman et al., *Tetrahedron Lett.*, 27, 4909 (1986).
6. The 5,6(2,3)-Endo-endo cis proton coupling constant is about 6–7 Hz, while the coupling constants for the corresponding exo-exo cis and endo-exo trans are 9–10 and 2.5–5 Hz, respectively, in the bicyclo[2.2.1]heptane model, see Reference 7(a). The coupling constant for the 5,6-trans protons in 2,8-dioxabicyclo[3.2.1]octane system was reported to be 2 Hz (see Reference 7(b)).
7. (a) Pretsch et al., "Tables of Spectral Data for Structure Determination of Organic Compounds," 2nd edition, Springer Verlag, p. H190, (1983); (b) Wilson et al., *J. Org. Chem.*, 57, 7151 (1992).
8. Witten et al., *Biochem. Biophys. Res. Commun.*, 124, 350 (1984).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The substantially pure compound MT 332, free of the cellular debris of the marine bryozoan *Myriapora truncata*, having the following chemical structures (in equilibrium):

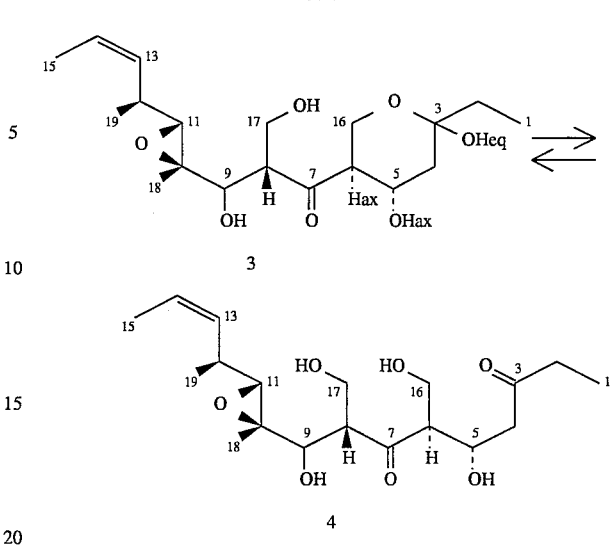

and the following physical properties; $[\alpha]_D^{26}$+44.6° (c. 0.06, MeOH); FABMS m/z 337 (M+H-2H$_2$O)$^+$, 395 ([M+Na]$^+$) and 411 ([M+K]$^+$); HRFABMS found 411.1784, calcd. for $C_{19}H_{32}O_7K$, 411.1785, Δ+0.1 mDa; found 395.2054, calcd. for M+Na, $C_{19}H_{32}O_7Na$, 395.2046, Δ-0.9 mDa; found 337.2019, calcd. for M+H-2H$_2$O, $C_{19}H_{29}O_5$, 337.2015, Δ-0.4 mDa); MS/MS: m/z 411→39; m/z 395→23; and the $^1$H and $^{13}$C NMR data for Compound 3 as shown in Table 3.

2. A pharmaceutical or veterinary composition comprising an effective antitumor amount of the substantially pure compounds designated herein as MT 332 and having the following structures:

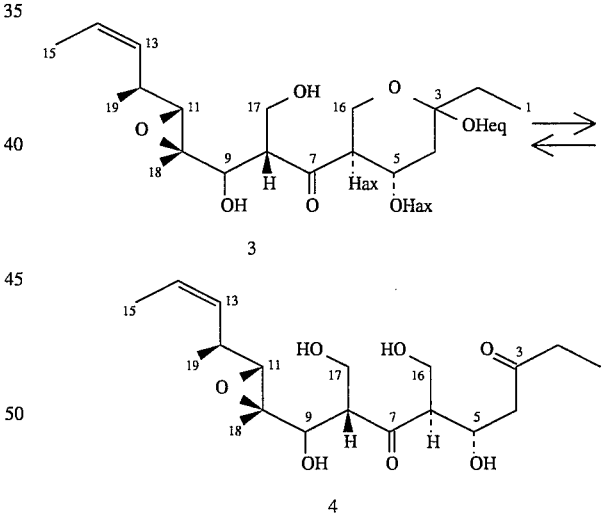

and a pharmaceutically acceptable carrier, diluent or excipient, wherein the tumor is selected from the group consisting of mammalian leukemia, mammalian melanoma and mammalian nasopharyngeal cancer.

3. A method of treating a patient suffering from a mammalian tumor selected from the group consisting of mammalian leukemia, mammalian melanoma and mammalian nasopharyngeal cancer, comprising administering to said patient, an effective antitumor amount of the substantially pure compounds designated herein as MT 332 and having the following structures:

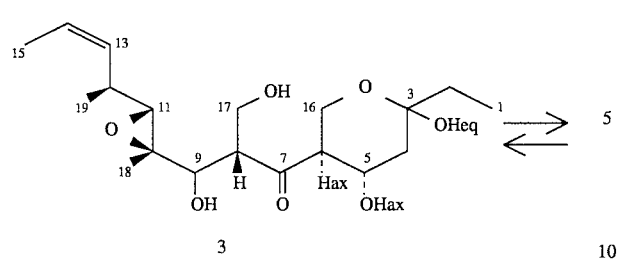
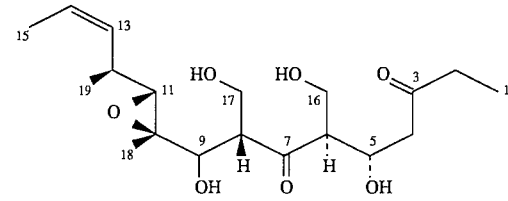
and a pharmaceutically acceptable carrier, diluent or excipient.
* * * * *